United States Patent [19]

Berg

[11] Patent Number: 5,236,005
[45] Date of Patent: Aug. 17, 1993

[54] QUICK CONNECT WALL OUTLET FOR MEDICAL GAS SERVICE OUTLET

[75] Inventor: Donald E. Berg, Avon Lake, Ohio

[73] Assignee: Tri-Tech Medical, Inc., Avon, Ohio

[21] Appl. No.: 938,291

[22] Filed: Aug. 31, 1992

[51] Int. Cl.[5] .............................................. F16L 5/00
[52] U.S. Cl. .................................. 137/360; 137/329.1
[58] Field of Search ............................. 137/360, 329.1

[56] References Cited

U.S. PATENT DOCUMENTS

| | | | |
|---|---|---|---|
| 2,742,052 | 4/1956 | McKee | 137/329.1 |
| 2,905,487 | 9/1959 | Schifter | 137/329.1 |
| 3,170,667 | 2/1965 | Szohatzky | 137/360 |
| 3,441,046 | 4/1969 | Cranage | 137/329.1 |
| 3,544,257 | 12/1970 | Cranage | 137/360 |
| 3,563,267 | 2/1971 | Thompson | |
| 3,931,829 | 1/1976 | McWhinnie, Jr. | 137/329.1 |
| 4,123,089 | 10/1978 | Viero et al. | 137/329.1 |
| 4,190,075 | 2/1980 | Kayser | |
| 4,344,455 | 8/1982 | Norton et al. | |
| 4,527,587 | 7/1985 | Fairlamb | |
| 4,562,856 | 1/1986 | Garvey et al. | |
| 4,718,699 | 1/1988 | Kulish et al. | |
| 4,844,409 | 7/1989 | Lackler et al. | |
| 4,915,132 | 4/1990 | Hodge et al. | |

*Primary Examiner*—A. Michael Chambers
*Attorney, Agent, or Firm*—Watts, Hoffmann, Fisher & Heinke Co.

[57] ABSTRACT

A wall outlet comprising an index plate, a closure member connected to the index plate, and a connector valve for connection to a medical gas adaptor. The valve is connected to a backside of the index plate and is accessible from the front of the outlet when the closure member is removed. Once the closure member is removed from the index plate, the valve parts can be removed from the wall outlet for service and repair such as replacement of a spring or O-ring without removal of the index plate.

9 Claims, 4 Drawing Sheets

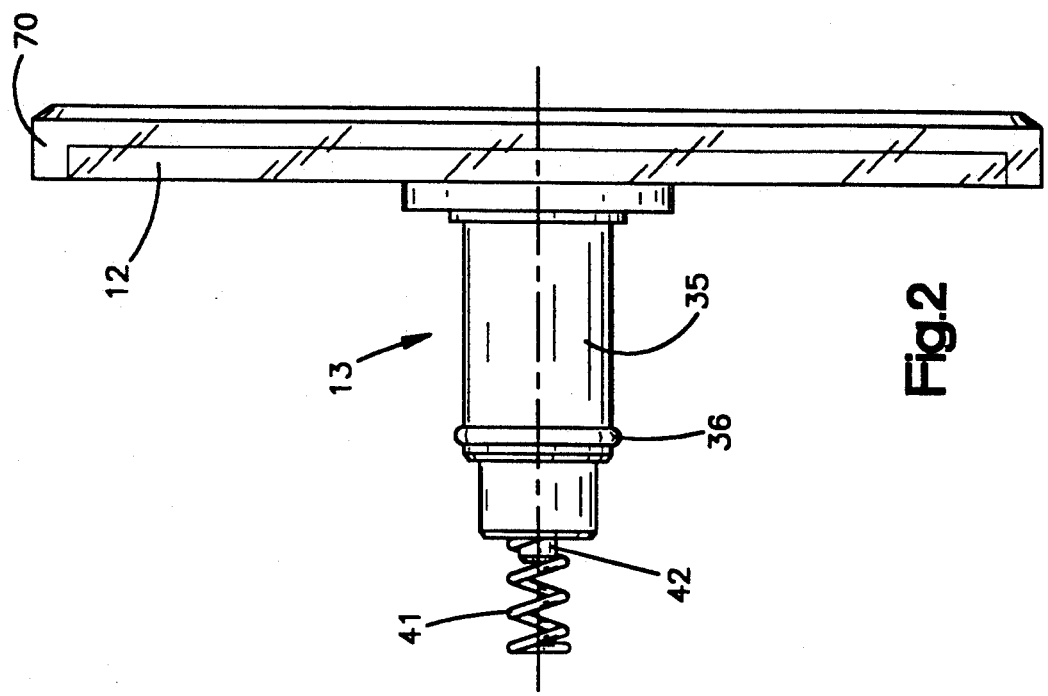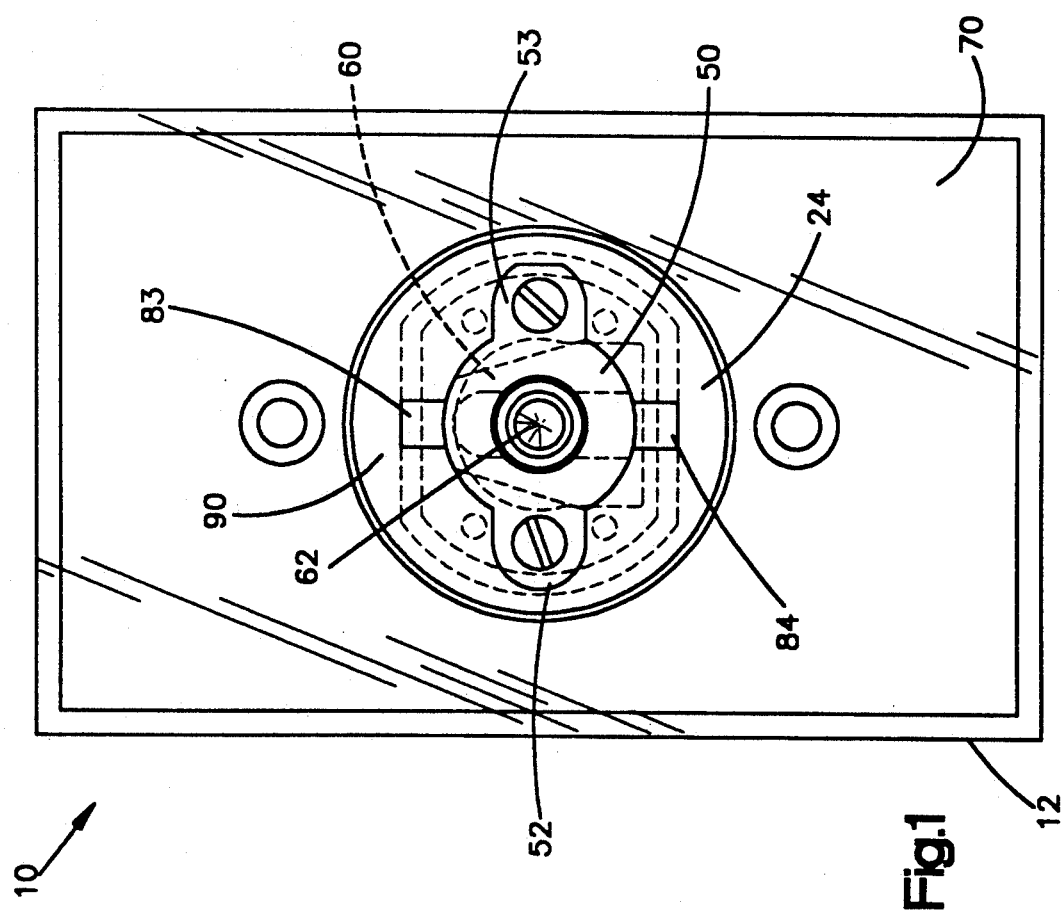

QUICK CONNECT WALL OUTLET FOR MEDICAL GAS SERVICE OUTLET

TECHNICAL FIELD

This invention relates to medical gas service outlets and, more particularly, to a quick connect wall outlet which is constructed in a manner that facilitates repair and replacement of internal valve parts.

BACKGROUND OF THE INVENTION

Medical gas service outlets are common in hospital rooms where gas services such as oxygen, air and nitrous oxide, as well as vacuum service, can be provide. A user can conveniently plug in the various equipment that utilizes the particular service with a specially designed, keyed adaptor that generally is connected to medical tubing for delivery to its end use device.

The typical adaptor is a quick-disconnect type device that serves to open a valve mechanism when inserted into the outlet. The adapter includes a release knob that can be rotated between a first position where a locking spring retains the adaptor within the service outlet, and a second position where the adaptor is released from the service outlet.

The conventional service outlet includes a spring biased plunger valve that is actuated by insertion of the adaptor to open the valve. The valve includes a seal assembly having an O-ring that seals around the nose of the adaptor and a hair pin spring that engages and releasably locks the nose of the adaptor. The spring that biases the plunger, the O-ring and the hair pin locking spring are subject to wear and require replacement.

One conventional service outlet in use today has a face plate assembly wherein a valve is attached to the back side of the assembly and a back cover is riveted into place to secure the valve in position. In order to replace the internal valve parts, the rivets have to be drilled out to remove the back cover. It is then necessary to rivet the back cover into place to reassemble the outlet. Since this is a difficult and time-consuming repair operation, many users simply replace the entire face plate assembly.

An improved medical service outlet has screws which hold the back cover in place. Although this construction offers some improvement over the riveted one, it is still necessary to remove the entire face plate assembly from the wall, and then remove the screws in order to replace parts within the valve. The repair operation remains an awkward and time-consuming procedure.

SUMMARY OF THE INVENTION

An object of the present invention is to provide an improved medical service outlet of the type described which is constructed to permit easy and quick replacement of internal valve parts and other elements.

A more specific object of the invention is to provide an improved medical service outlet of the type described that is characterized by a front opening that provides access to internal valve parts and other elements, and a removable closure member for the opening, the closure member being held in place by a pair of screws so that the member can be removed from the front of the outlet.

Another object of the invention is to provide an improved medical gas outlet of the type described that is characterized by a face plate that surrounds the wall opening, an index plate that is separate from the face plate and is removable from the front of the outlet, and a valving mechanism carried by the index plate.

A further object of the invention is to provide a medical gas outlet as described in the previous paragraph that is further characterized by an access opening in the front of the index plate permitting the valving mechanism parts and other parts to be withdrawn and replaced from the front of the outlet, and a removable closure member for the opening mounted in the front face of the index plate.

Still another object of the invention is to provide a self-contained index plate and plunger valve mechanism for a medical gas outlet characterized by an access opening in the front face of the plate that permits the valve mechanism parts and other elements to be removed and replaced, and a removable closure member for the opening mounted in the front face of the plate.

The foregoing objects are attained and the disadvantages of the prior art are overcome by a construction that forms the front part of a medical gas service outlet comprising an index plate having front and back faces, an open-end valve housing attached to the back face, a reciprocal valve member and coil spring assembly in the housing, and a seal assembly in the front end opening of the housing. An access opening in the front face provides access to the seal assembly. A removable closure member is fitted into the access opening from the front face and has a through hole aligned with the valve member, whereby the nose of a quick-disconnect adaptor can be inserted into actuating engagement with the valve member. A hair pin spring is mounted behind the closure member in position to be engaged by the nose of the adaptor. The closure member is removably fastened to the index plate so that the closure member can be withdrawn from the front of the index plate to access the hair pin spring, the seal assembly and the plunger and coil spring assembly. The index plate and valve mechanism are separate from a face plate of the outlet so that the index plate and valve mechanism can be removed and replaced as a unit, if desired, without disturbing the rest of the outlet.

As will be apparent from the foregoing, the new construction facilitates replacement of internal parts from the front of the outlet. This is accomplished by removing the closure member from the front of the index plate. In the preferred embodiment, the closure member is held in place by a pair of screws. Once the closure member is removed, the internal valve parts can be removed from the front of the outlet without removing it from the wall. This allows for quick and easy replacement of the hair pin spring, the O-ring and the plunger spring without removal of the index plate.

Other advantages and a fuller understanding of the invention will be had from the following detailed description and the accompanying drawings.

BRIEF DESCRIPTION OF THE DRAWINGS

FIG. 1 is a front elevational view of a medical gas service wall outlet according to the preferred embodiment of the present invention;

FIG. 2 is a side elevational view of a front unit according to the preferred embodiment of the present invention;

DETAILED DESCRIPTION OF THE PREFERRED EMBODIMENT

Figure 3:
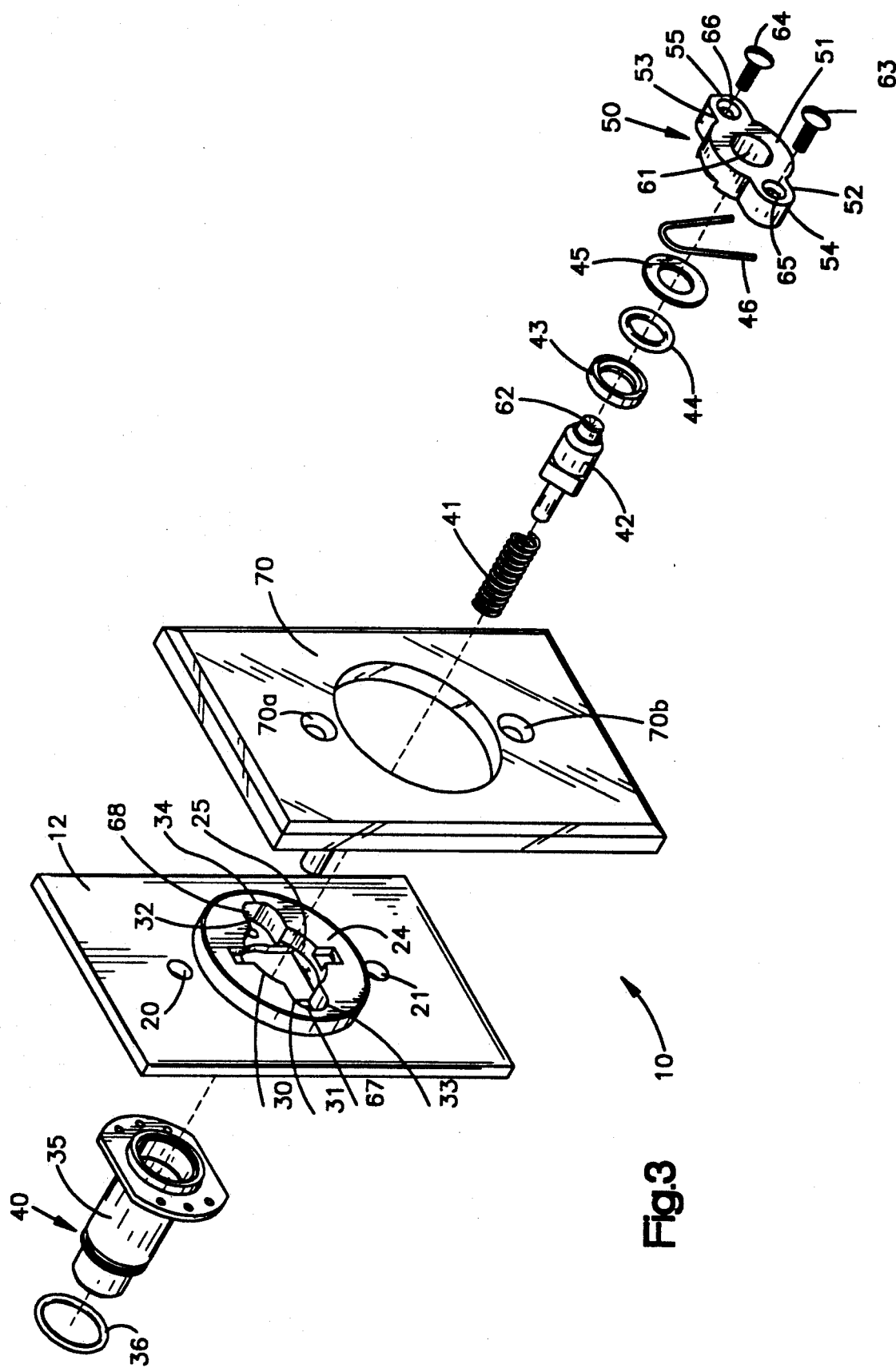
FIG. 3 is an exploded view of the front unit according to the preferred embodiment of the present invention.
Figure 4:
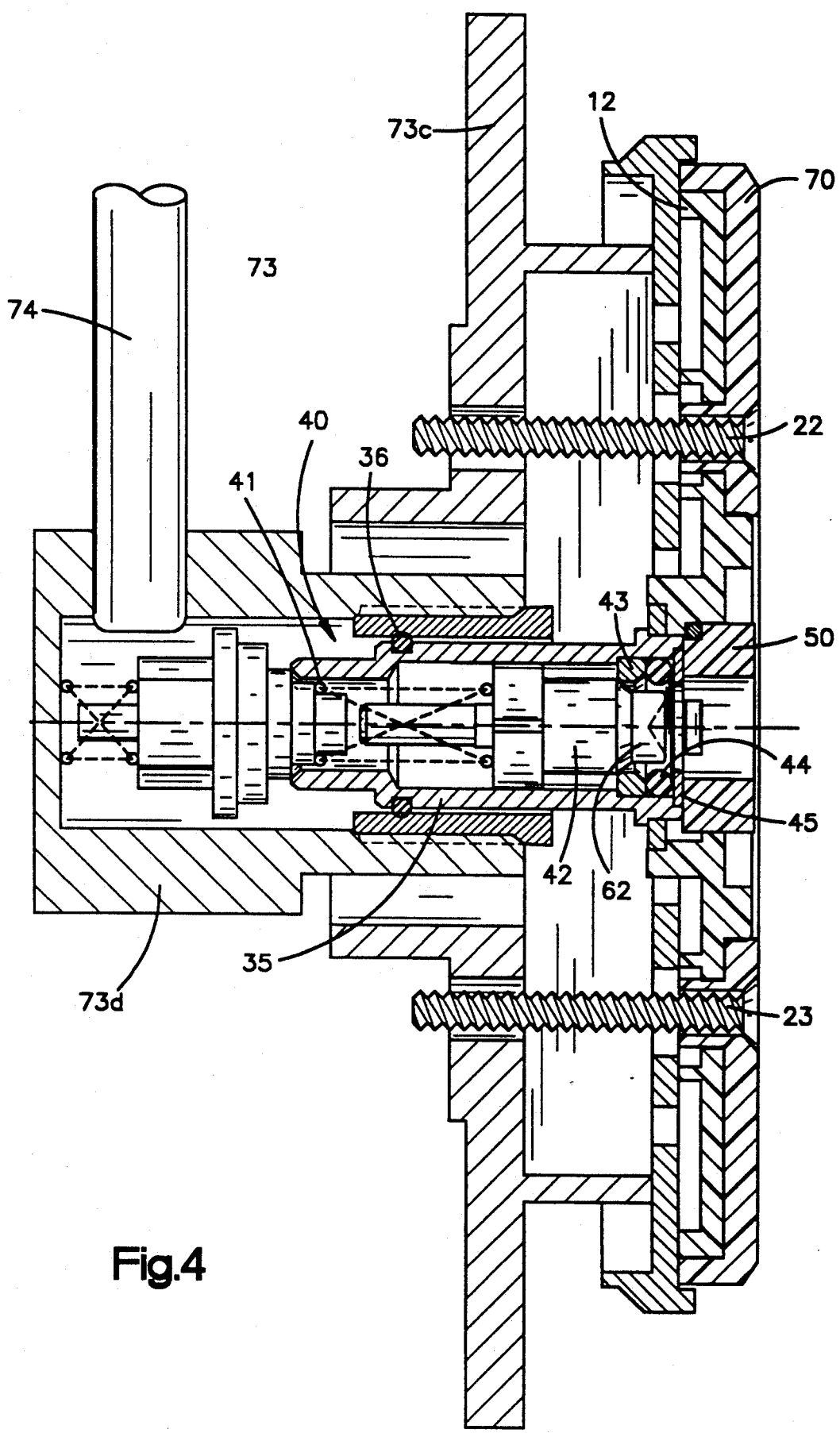
FIG. 4 is a sectional view of the medical gas service wall outlet according to the preferred embodiment of the present invention as seen from the plane indicated by the line 4—4 of FIG. 1; and, FIG. 5 is an exploded view of the medical gas service wall outlet according to the preferred embodiment of the present invention.

Referring to the drawings, a wall outlet 10 for use as a medical gas service outlet is illustrated. The wall outlet comprises a face plate housing 11, an index plate 12 and a connector valve 13. The connector valve 13 is of the type typically referred to as a poppet valve.

The index plate 12 defines two bores 20, 21 for receiving screws 22, 23, respectively. The index plate 12 has a raised, circular central portion 24. The central portion 24 defines a cavity 25. The cavity 25 has a large, circular portion 30 flanked by outer portions 31, 32. The outer portion 31 is rounded at an outer edge portion 33, while the outer portion 32 is flat at an outer edge portion 34.

The valve 13 includes a open-ended valve housing 35 that has a first O-ring 36 placed around a distal end 40 of the assembly. A plunger spring 41 is placed within the assembly and a reciprocatable plunger 42 is placed adjacent to the spring 41 within the assembly. The plunger spring 41 biases the plunger 42 towards the front of the valve when the valve is assembled. Seal assembly 91 includes a seal bushing 43, a second O-ring 44 and a washer 45. Seal bushing 43 is placed adjacent to the plunger 42 and a second O-ring 44 is placed adjacent the seal bushing 43. A washer 45 is placed adjacent the second O-ring 44 and a hair pin spring 46 is then placed adjacent the washer 45.

The open-ended valve housing 35 is connected to a backside of the index plate 12 such that the open-ended valve housing 35 is aligned with the circular portion 30. Once the other parts of the valve 13 are placed within the housing 35 as illustrated in FIG. 3, a closure member 50 is placed within the cavity 25.

The closure member 50 is shaped to correspond to the shape of the cavity 25. The member 50 has a central circular portion 51 that is flanked by outer portions 52, 53. The outer portion 52 is rounded at an outer edge portion 54, while the outer portion 53 is flat at an outer edge portion 55. The outer edge portions 33, 34 of the cavity 25 provide structure that cooperates with the outer edge portions 54, 55 of the closure member 50 to assure that the member can only be placed within the cavity in a correct orientation. It is important that the closure member be placed correctly within the cavity in that a backside of the member 50 defines a groove 60 (illustrated in phantom in FIG. 1) that orients the hair pin spring 46 correctly. The hair pin spring is oriented in an inverted U-shape as illustrated in FIG. 1 and the groove 60 corresponds to such orientation.

The closure member 50 defines a large central throughbore 61 that serves as the opening for the valve 13. A head 62 of the plunger 42 projects into the throughbore 61 when the valve is assembled and the member is in place.

Once the closure member 50 is placed within the cavity 25, two screws 63, 64 are placed within bores 65, 66 defined within the closure member 50 and bores 67, 68 defined within the index plate 12.

Figure 5:
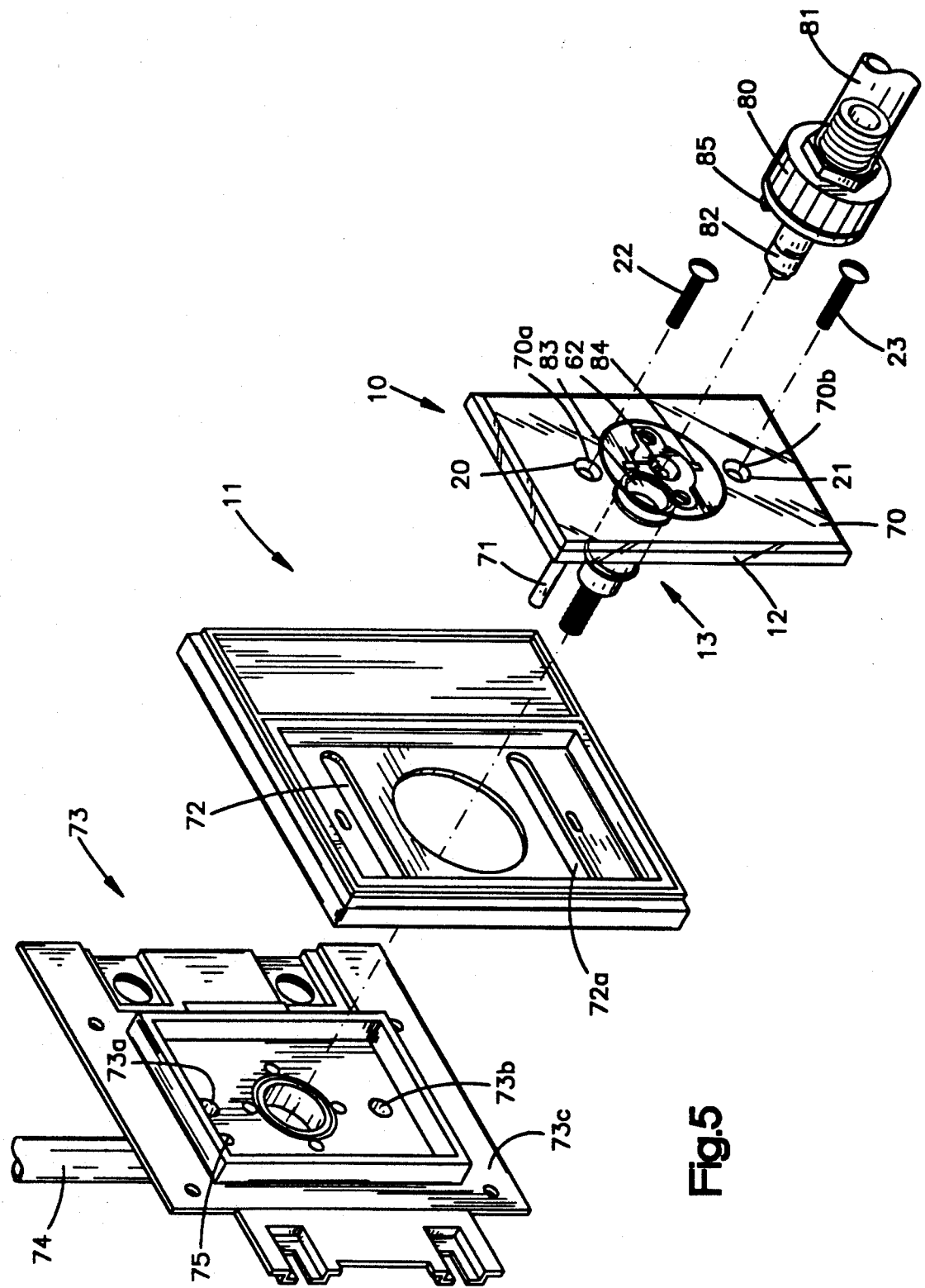

As best seen in FIG. 3, to complete the wall outlet 10, a clear nameplate cover 70 is placed over the index plate 12. As seen in FIG. 5, the index plate 12 is then placed within face plate housing 11 to form a face plate assembly that serves as a front unit for the outlet 10. An indexing pin 71 located on the backside of the index plate is placed through an oblong bore 72 defined within the face plate housing. The face plate housing, index plate and nameplate cover are then placed over a gas source assembly 73 that is mounted in the wall of a room. The gas source assembly 73 is generally of the type disclosed in U.S. Pat. No. 3,563,267, which is incorporated herein in its entirety by reference. The assembly 73 includes a wall plate 73c, a valve housing 73d connected to the wall plate and a gas inlet tube 74 connected to the valve housing. The inlet tube 74 is connected to a source (not shown) of medical gas or a vacuum source as required by an end use device. The valve housing houses a valve for controlling the supply of gas from the source. The indexing pin 71 is placed within a bore 75 defined within the gas source wall plate 73c and helps assure proper orientation of the index plate relative to the gas source assembly. Additionally, the indexing pin assures that only the proper index plate 12 is utilized with the gas source wall plate 73c. The screws 22, 23 are placed through the bores 20, 21, as well as bores 70a, 70b, 72, 72a and 73a, 73b in order to hold all of the plates together and thereby complete the wall outlet.

Once the wall outlet is assembled, an adaptor 80 that is attached to medical gas tubing 81 is inserted into the outlet with a nose portion 82 of the adaptor 80 entering the opening 53 defined within the closure member 50. The adaptor 80 is generally of the type disclosed in U.S. Pat. No. 4,844,409, which is incorporated herein in its entirety by reference. The nose portion 82 engages the plunger head 62 forcing it back against the spring 41, thereby opening the valve within the gas source assembly 73 and placing the adaptor 80 in fluid communication with the gas source. The second O-ring 44 seals around the nose 82 while the hair pin spring 46 engages and releasably secures the nose of the adaptor.

If it is necessary to provide service to the valve, such as replacing the plunger spring 41, the second O-ring 44 or the hair pin spring 46, instead of replacing the entire index plate or face plate assembly, including the valve, or dismantling the entire wall outlet, all that needs to be done is to remove the two screws 63, 64 and remove the closure member 50. This allows the valve parts to be removed, specifically plunger spring 41, plunger 42, seal bushing 43, the second O-ring 44, the washer 45 and the hair pin spring 46. Once finished, the valve is reassembled and the closure member 50 is replaced.

Two recesses 83, 84 are defined within the raised central portion 90. The arrangement of these recesses varies depending on the type of gas service that is to be supplied at the outlet 10. Corresponding flanges (one shown at 85) on the adaptor 80 for engagement with the recesses is provided thereby assuring that only appropriate end use devices will be used with the wall outlet 10. As stated previously, the indexing pin assures that only the proper index plate 12 is utilized with the gas source wall plate 73c.

Although the preferred embodiment of this invention has been shown and described, it should be understood that various modifications and rearrangements of the parts may be made without departing from the scope of the invention as disclosed and claimed herein.

I claim:

1. A self-contained unit forming the front part of a medical gas service outlet comprising:

a. an index plate having front and back faces;

b. an open-end valve housing attached to said back face;

c. a reciprocal valve member and coil spring assembly in said housing;

d. a seal assembly in the front end opening of said housing;

e. an access opening in said front face providing access to said seal assembly;

f. a removable closure member fitted into said access opening from said front face, said closure member having a through hole aligned with said valve member, whereby a nose of a quick-disconnect adaptor can be inserted into actuating engagement with said valve member;

g. a hair pin spring mounted behind said closure member in position to be engaged by said nose of said adaptor; and h. means removably fastening said closure member to said index plate so that said closure member can be withdrawn from the front said index plate to access said hair spring, said seal assembly and said reciprocal valve member and coil spring assembly.

2. The wall outlet of claim 1 further comprising cooperative structure on said closure member and said index plate for assuring proper alignment of said closure member when said closure member is connected to said index plate.

3. For use in a medical gas service outlet, a self-contained unit comprising:

a. an index plate having front and back faces, a cavity which opens on said front face, and a hole through said back face opening into the bottom of said cavity;

b. an open-ended valve housing attached to said back face of said index plate, said valve housing having its forward end projecting into said hole of said index plate, whereby the interior of housing is in open communication with said cavity;

c. a reciprocal plunger valve and biasing spring in said valve housing;

d. a seal assembly including a seal bushing, a washer and an O-ring between said washer and said seal bushing, said seal assembly being mounted in the forward end of said valve housing;

e. a removable closure member closing the mouth of said cavity, said member having a through opening adapted to receive a nose of an adaptor for engagement with said plunger valve;

f. a hair pin spring in said cavity behind said closure member having its legs on opposite sides of said through opening; and g. said plunger valve, biasing spring seal, assembly and hair pin spring being removable from said unit when said cavity is open;

h. means removably securing said closure member to said index plate for providing access to said plunger valve, biasing spring, seal assembly and hair pin spring from said front face of said index plate.

4. In a medical gas service outlet including a wall plate, a valve housing attached to the rear face of said wall plate, a gas inlet tube connected to said valve housing, and valve means in said valve housing, the improvement comprising:

a. an index plate;

b. a tubular plunger housing having open ends attached to and extending from the back of said index plate in position to project into said valve housing;

c. a plunger valve reciprocally mounted in said plunger housing for actuating said valve means;

d. a coil spring in said plunger housing between said plunger valve and said valve means;

e. a cavity in said index plate opening on its front face;

f. said cavity having an opening in its bottom that receives the forward open end of said plunger housing;

g. a seal assembly including a seal bushing, an O-ring and a washer in the forward open end of said plunger housing;

h. a removable closure member having a hole therethrough fitted in the mouth of said cavity;

i. a hair pin spring mounted behind said member in the bottom of said cavity; and j. means removably securing said closure member to said index plate for providing access to said hair pin spring, said seal assembly, said plunger valve and said coil spring from the front of said index plate.

5. In a medical gas service outlet including a wall plate, a valve housing attached to the rear face of said wall plate, a gas inlet tube connected to said valve housing, and valve means in said valve housing, the improvement comprising:

a. an index plate having front and back faces;

b. an open-ended plunger housing at said back face;

c. a movable plunger valve biased by a biasing spring mounted in said plunger housing so that inward movement of said plunger valve can actuate said valve means;

d. a seal assembly including an O-ring in the forward end of said plunger housing;

e. an access opening in said front face of said index plate providing access to said plunger valve, said biasing spring and said seal assembly;

f. a removable closure member mounted in said access opening, said closure member having a through hole for permitting a nose of a quick-disconnect adaptor to be inserted into actuating engagement with said plunger valve;

g. a hair pin spring behind said closure member for lockingly engaging the inserted nose of the adaptor; and h. fastening means on front of said index plate for removably attaching said closure member thereto, whereby said closure member can be withdrawn from the front of said index plate to access said hair pin spring, said seal assembly, said plunger valve and said biasing spring.

6. A front unit of a wall outlet for receiving a medical gas adaptor connected to a gas tubing in order to provide a supply of medical gas or a vacuum source, said unit comprising:

a. an index plate;

b. a connector valve for connection to said adaptor, said valve being connected to said index plate; and, c. a closure member removably connected to a front face of said index plate to provide access to said connector valve from the front of said front unit when said closure member is removed.

7. The front unit of claim 6 further comprising cooperative structure on said closure member and said index plate for assuring predetermined alignment of said closure member when said closure member is connected to said index plate.

8. The front unit of claim 7 wherein said connector valve comprises:
 a. a open-ended valve housing;
 b. a first O-ring around a distal end of said valve housing;
 c. a plunger spring placed within said valve housing;
 d. a plunger adjacent said spring;
 e. a seal bushing adjacent said plunger;
 f. a second O-ring adjacent said bushing;
 g. a washer adjacent said second O-ring; and,
 h. a hair pin spring adjacent said washer and said index plate.

9. The front unit of claim 6 wherein said connector valve includes a plunger, a plunger biasing spring, and a seal assembly, said plunger, biasing spring, and seal assembly being accessible from said front face of said index plate when said closure member is removed from said index plate.

* * * * *